United States Patent
Bazer-Bachi et al.

(10) Patent No.: US 10,441,933 B2
(45) Date of Patent: Oct. 15, 2019

(54) REDUCED-CAPACITY MOVING-BED REACTOR WITH RADIAL FLOW OF THE FEEDSTOCK

(71) Applicant: IFP Energies nouvelles, Rueil-Malmaison (FR)

(72) Inventors: Frederic Bazer-Bachi, Irigny (FR); Fabian Lambert, Chatou (FR); Cecile Plais, Les Haies (FR)

(73) Assignee: IFP Energies Nouvelles, Rueil-Malmaison (FR)

(*) Notice: Subject to any disclaimer, the term of this patent is extended or adjusted under 35 U.S.C. 154(b) by 111 days.

(21) Appl. No.: 15/381,807

(22) Filed: Dec. 16, 2016

(65) Prior Publication Data
US 2017/0173549 A1    Jun. 22, 2017

(30) Foreign Application Priority Data
Dec. 17, 2015 (FR) .................................. 15 62672

(51) Int. Cl.
| | |
|---|---|
| *B01J 8/12* | (2006.01) |
| *C10G 35/12* | (2006.01) |
| *B01J 8/08* | (2006.01) |
| *C07C 1/24* | (2006.01) |
| *C07C 5/27* | (2006.01) |
| *C07C 6/04* | (2006.01) |
| *C10G 11/00* | (2006.01) |

(52) U.S. Cl.
CPC . *B01J 8/08* (2013.01); *B01J 8/12* (2013.01); *C07C 1/24* (2013.01); *C07C 5/2702* (2013.01); *C07C 6/04* (2013.01); *C10G 11/00* (2013.01); *C10G 35/12* (2013.01); *B01J 2208/00752* (2013.01); *B01J 2208/00761* (2013.01)

(58) Field of Classification Search
CPC ................................... B01J 8/12; C10G 35/12
See application file for complete search history.

(56) References Cited

U.S. PATENT DOCUMENTS

| | | | | |
|---|---|---|---|---|
| 3,799,866 A | * | 3/1974 | Lengemann | B01J 8/125 208/139 |
| 4,033,727 A | * | 7/1977 | Vautrain | B01J 8/0085 208/146 |
| 4,277,444 A | * | 7/1981 | Van Landeghem | B01J 8/003 422/634 |

(Continued)

FOREIGN PATENT DOCUMENTS

| | | | | |
|---|---|---|---|---|
| FR | 841008 A1 | 5/1939 | | |
| FR | 2953738 A1 | 6/2011 | | |
| WO | WO-03002245 A1 | * 1/2003 | | B01J 8/10 |

OTHER PUBLICATIONS

French Search Report dated Aug. 1, 2016, issued in corresponding FA818727, 7 pages.

(Continued)

*Primary Examiner* — Jennifer A Leung
(74) *Attorney, Agent, or Firm* — Millen, White, Zelano & Branigan, PC

(57) ABSTRACT

This invention describes a moving-bed catalyst reactor having radial flow of the feedstock called moving-bed radial reactor, consisting of 3 zones called upper hemispheric body (III), lateral zone (II), and lower hemispheric body (I), the three zones being connected together by means of flanges.

5 Claims, 1 Drawing Sheet

(56) References Cited

U.S. PATENT DOCUMENTS

| | | | | |
|---|---|---|---|---|
| 4,567,023 A | * | 1/1986 | Greenwood | B01J 8/003 |
| | | | | 208/169 |
| 4,743,432 A | * | 5/1988 | Vollhardt | B01J 8/0453 |
| | | | | 422/148 |
| 5,015,383 A | * | 5/1991 | Evans | B01J 8/0214 |
| | | | | 100/295 |
| 5,209,908 A | * | 5/1993 | Koves | B01J 8/003 |
| | | | | 208/113 |
| 2006/0269461 A1 | * | 11/2006 | Scanlon | B01J 8/008 |
| | | | | 422/218 |
| 2009/0154632 A1 | * | 6/2009 | Naunheimer | B01D 53/0431 |
| | | | | 376/210 |
| 2009/0324465 A1 | | 12/2009 | Stewart et al. | |
| 2011/0070149 A1 | * | 3/2011 | Douziech | B01J 8/009 |
| | | | | 423/594.19 |

OTHER PUBLICATIONS

English translation Abstract of FR2953738A1 published Jun. 17, 2011 (1 page).

\* cited by examiner

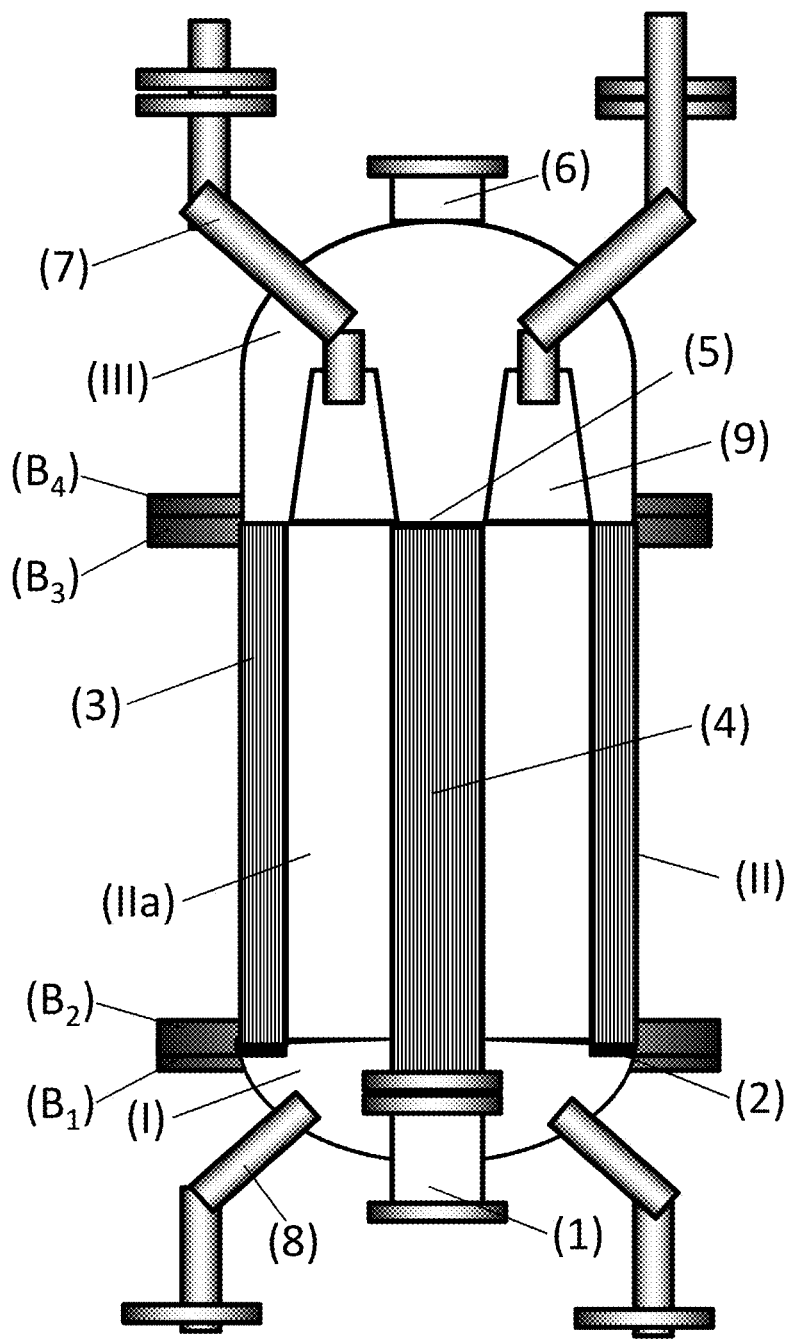

REDUCED-CAPACITY MOVING-BED REACTOR WITH RADIAL FLOW OF THE FEEDSTOCK

BACKGROUND OF THE INVENTION

A certain number of refining and petrochemical methods rely on reactors that are called radial reactors. Among these methods, it is possible to cite—without being limiting—the catalytic reforming of gasolines, oligocracking of olefinic cuts, dehydration of alcohols (ethanol, propanol, isobutanol), skeletal isomerization of olefins, metathesis for the production of propylene, dehydrogenation of paraffins.

In a radial-bed reactor, the catalytic bed has the shape of a vertical cylindrical annulus that on the interior side is bounded by an interior screen, called screen of the central collector, retaining the catalyst, and on the exterior side, either by another screen of the same type as the interior screen and called outer screen, or by a device consisting of an assembly of scallop-shaped screen elements (called "scallops" in English terminology).

This reactor geometry is that which is used predominantly in the industry, but it necessitates an outer screen/minimum central collector space to ensure that, during maintenance operations on the reactors, the operators can go between the screens so as to inspect them and to clean them (fragments of catalysts deposited between the screens).

The current sizing regulations call for two criteria that can prove contradictory for radial beds: a minimum catalytic bed thickness of about 400 mm so as to achieve the minimum boundary for the maintenance of the screens, and a minimum pressure drop in going through the bed of between 20 and 80 mbars (mbar is the abbreviation for millibar or $10^{-3}$ bar) in the interior of the radial bed to maintain a proper distribution of the gas in the catalytic bed, without blocking the flow of the catalyst.

Now, for the reduced capacities of reactors, maintaining a sufficient pressure drop for proper distribution of the feedstock over the entire height of the reactor implies shortening the bed (increasing superficial velocities).

Furthermore, below a certain critical capacity, this shortening is limited by the minimum thickness of 400 mm, not making it possible to maintain the pressure drop criterion. Therefore, a need exists for a technological solution that makes it possible to be free of at least one of the two criteria, optionally both, so as to maintain the possibility of sizing the radial beds, in particular moving beds, for the reduced capacities.

BRIEF DESCRIPTION OF DRAWING

FIG. 1 shows a diagrammatic view of a moving-bed radial reactor according to the invention.

In the prior art relating to radial-bed reactors, it is possible to cite the U.S. Pat. No. 6,221,320, which provides a rather complete summary of the conventional technologies.

According to the state of the art, the catalytic bed in a moving-bed radial reactor is defined by two screens, an inner screen and an outer screen. More specifically, a distinction is generally made between:

An inner screen that defines the central collector of the gaseous effluents,

An outer screen that defines the space for supplying the feedstock in the gaseous state.

The processed fluid arrives by the outer space that is defined between the shell ring and the outer screen. It then passes through the catalytic bed in a manner that is approximately horizontal and perpendicular to the circulation of the catalyst that is gravitational, i.e., approximately vertical from top to bottom, and is obtained as a result of the weight alone of the catalyst bed.

The processed fluid in radial flow and the catalyst in gravitational flow are separated by the inner screen that generally has a cylindrical shape, with the same approximately vertical axis as the outer screen.

The cylinder, or more generally the approximately cylindrical shape, defined by the inner screen, serves as central collector to drain the gaseous effluents from the reaction zone that is between the outer screen and the inner screen and therefore of approximately annular shape.

The constraints linked to the moving-bed radial technology are numerous. In particular, the gas velocities in going through the catalytic bed are limited in order to:

avoid cavitation on input to the bed, avoid blocking of the catalyst at its exit against the inner screen, reduce the pressure drops based on the velocity and the thickness of the bed.

For reasons of uniform distribution over the entire height of the catalytic bed, a perforated tube designed to create the pressure drop can be added onto the central collector.

Finally, for construction reasons, it is often necessary to leave a sufficient space between the inner screen and the outer screen. Ultimately, when all of the constraints for this reactor configuration are accumulated, the minimum volume of catalyst that can be enclosed in the annular zone cannot fall below a certain minimum value.

Generally, according to the prior art, the maximum accessible PPH in radial moving beds are on the order of 20 $h^{-1}$, whereas the reactor according to this invention makes it possible to reach PPH of higher than 50 $h^{-1}$, even higher than 100 $h^{-1}$.

SUMMARY DESCRIPTION OF THE INVENTION

This invention describes a small-size reactor having a moving bed and radial flow of the feedstock.

Moving bed is defined as a bed that flows gravitationally, often at slow velocity, on the order of one meter per hour, and in an approximately vertical direction.

This type of flow is encountered in many reactors, particularly reactors used for the catalytic reforming of gasolines that requires a stage for complex regeneration of the catalyst.

Finally, small size is defined as reactors whose thickness of the catalytic bed, i.e., the radial dimension between the outer screen and the central collector, is between 100 and 400 mm.

More specifically, the reactor according to this invention can be defined as a moving-bed reactor, having a radial flow of the feedstock and having a gravitational flow of the catalyst that is made up of 3 units called upper hemispheric body (III), lateral zone (II), and lower hemispheric body (I).

Overall, this reactor has a cylindrical symmetry around its approximately vertical central axis.

The upper hemispheric body (III) is provided with an intake pipe (6) for the feedstock and with legs (7) for introducing the catalyst communicating with conical elements (9) that provide access to the annular zone (IIa) located between the central collector (4) and the outer screen (3). The conical elements (9) form a space that is cone-shaped and that is of the same cylindrical symmetry as the reactor itself. The central collector (4) is equipped on its outer face with a screen of the same type as the exterior screen (3). It is closed at its upper end by a solid plate (5).

The outer screen (3) is positioned parallel to the lateral wall (II) of the reactor at a certain distance from the latter, and the central collector (4) extends approximately along the longitudinal axis of symmetry of the reactor over the entire height of the annular zone (IIa) and continues over a certain height inside the lower hemispheric body (I).

A certain space (not shown in FIG. 1) is furnished between the lateral wall (II) and the outer screen (3).

The outer screen (3) rests on a supporting ring (2) that is preferably attached to the wall of the lower hemispheric body (I).

In certain cases, this outer screen (3) can consist of an assembly of scallop-shaped screen elements, extending longitudinally over the entire height of the annular zone (IIa).

The annular zone (IIa) extends between the outer screen (3) and the central collector (4). This annular zone (IIa) corresponds to the catalytic zone over a radial distance of between 100 and 400 mm.

The height of said annular zone (IIa) generally corresponds to the height of the lateral zone (II), but can, in certain cases, go beyond into the lower (I) and upper (III) hemispheric bodies.

The feedstock passes through the annular zone (IIa) radially, i.e., in an approximately horizontal manner, from the outer screen (3) to the central collector (4), and the catalyst flows vertically from top to bottom of said zone.

The scope of the invention is observed if the feedstock passes through the radial bed in the opposite direction, i.e., from the center of the reactor to the periphery.

In this case, the central collector (4) acts as a distribution screen, and the outer screen (3) acts as a peripheral collector of the effluents.

The scope of the invention is also observed if the feedstock is brought through the pipe (1), and then drained through the pipe (6).

The lower hemispheric body (I) carries the drain legs (8) of the catalyst and the drain pipe (1) for the reaction effluents, the reactor being characterized in that the upper hemispheric body (III) is connected by the flanges B3, B4 to the lateral zone (II), and in that the lower hemispheric body (I) is connected by the flanges B1 and B2 to said lateral zone (II).

The flanges B1 to B4, whose sizing is well known to a person skilled in the art, will not be further described.

This invention also relates to any method using the previously-described moving-bed reactor.

Within the scope of the method of catalytic reforming of gasolines, cited here by way of example that is in no way limiting, the reactor according to the invention is generally positioned at the head of the series of reactors constituting the reforming unit, a method in which:
  the feedstock enters the reactor by means of the inlet pipe (6) located in the upper part (III) of the reactor and enters into the annular zone (IIa) located inside the lateral body (II) by passing through the outer screen (3),
  the feedstock passes through the catalytic bed contained in the annular zone (IIa) in an approximately radial manner, and the effluents resulting from the catalytic reaction are collected in the central collector (4), and then
  are drained from said reactor through the outlet pipe (1) situated on the lower hemispheric body (I),
  the catalyst is admitted into the annular zone (IIa) through one or more legs (7) that communicate with said annular zone through conical elements (9), the catalyst flows gravitationally into the annular zone (IIa), and then is drained from the reactor through drain legs (8) located in the lower hemispheric body (I).

Finally, this invention also relates to a method of constructing the reactor according to the invention, in which:
  a) the lower body (I) is equipped with drain legs (8) for draining the catalyst, and with a drain pipe (1) for reaction effluents that is provided at its upper end with a means that makes possible its reattachment to the central collector (4),
  b) the central collector (4) is positioned in the lateral body (II), and said central collector (4) is attached to the pipe (1) for draining the effluents,
  c) the central collector (4) is closed at its upper end by a solid plate (5),
  d) the lower body (I) is attached to the lateral body (II) by an assembly of flanges (B1) and (B2) carried by the lateral body (II) and the lower body (I),
  e) an outer screen (3) or outer screen elements are attached to a supporting ring (2) positioned in the unit formed by the lateral body (II) and the lower body (I),
  f) the upper body (III) is attached to the lateral body (II) by means of an assembly of flanges (B3) and (B4), said upper body (III) being previously equipped with a pipe (6) for introducing the feedstock and with lowering legs (7) making possible the entry of the catalyst into the reactor.

Thanks to the mounting by flanges according to the invention, it is very easily possible to remove the internals (outer screen (3) or screen elements and central collector (4)), and thus to inspect them and/or replace them and/or clean them.

The time necessary for these operations is therefore minimized in relation to the current reactor configurations, which do not make it possible to do the maintenance operations easily for the reduced capacities.

In the case of small-size reactors whose thickness of the catalytic bed is less than 400 mm, the solution according to the invention of dividing the reactor into 3 bodies (I), (II), and (III), and of assembling these bodies by flanges is the most efficient in relation to the maintenance aspect.

The following description is given with reference to FIG. 1.

The reactor has three parts:
  A lower body (I),
  A lateral body (II) also called the body of the reactor,
  An upper body (III).

Annular zone (IIa) is used to designate the catalytic zone contained in the lateral body (II).

The lower body (I), generally of hemispheric shape, also called the lower hemispheric body, comprises an outlet pipe (1) for the effluents that is located in said lower body and is closed near the shell ring in its upper part by the supporting ring (2).

This lower body (I) is equipped with a flange (B1) welded all along the approximately circular perimeter of said lower zone (I).

The supporting ring (2) is limited in its radial dimension to make possible the movement of the catalyst from the annular body (IIa) to the drain legs (8) located on the lower hemispheric body (I).

The supporting ring (2) is not always strictly situated in the area of the flange (B1, B2), but can be welded to the wall of the lower hemispheric body (I) or of the lateral body (II).

It can in certain cases be found, at least partly, in the lateral body (II).

The catalyst is introduced into the upper hemispheric body (III) through introduction legs (7) that are themselves in communication with the annular zone (IIa) by means of the conical parts (9).

The catalyst flows gravitationally into the annular zone (IIa), and then is taken up again by the drain legs (8) whose upper end is found in the lower hemispheric body (I).

The outer screen (3), positioned parallel to the lateral wall of the body (II), makes it possible to distribute the feedstock over the entire height of the lateral zone (IIa) so that it is placed in contact with all of the catalyst contained in the annular zone (IIa).

The feedstock passes through the annular catalytic zone (IIa) in an approximately radial manner, and the effluents are recovered in the central collector (4).

The upper part of the catalytic zone (IIa) is closed by the conical elements (9) that are generally bolted onto the central collector (4) and/or onto the outer screen (3).

Any other connection known to a person skilled in the art, to ensure the assembly of these conical elements (9), can also be used.

The upper part of the central collector (4) is closed by a solid plate (5).

The lateral body (II) is provided with a flange (B2) welded all along the lower part of the approximately circular perimeter of said lateral zone (II), and with a flange (B3) welded all along the upper part of said lateral zone (II).

The solid plate (5) is not necessarily situated in the area of the flange B3. In this case, connections can be put in place between the flanges and the solid plate (5) to facilitate the installation of said solid plate (5).

In the case where the solid plate (5) is situated approximately at the same level as the flange (B3), said solid plate (5) and the conical parts (9) are connected to the wall by assembly by means of an outer ring (not shown in FIG. 1).

Spaces must be provided on the periphery of the upper body (III) to allow the gas to pass to the space defined by the wall of the lateral body (II) and the outer screen (3), or the screen elements when it consists of elements (called "scallops" in English terminology).

The lateral body (II) is provided with a flange (B3) welded all along the top part of the approximately circular perimeter of said lateral zone (II).

The upper body (III) is also equipped with a flange (B4). The assembly of the flanges (B3) and (B4) is typically done by bolting, or by any other means known to a person skilled in the art.

The upper body (III) is provided with an intake pipe (6) for the feedstock and with the legs (7) for introducing the catalyst.

These legs (7) have their lower end communicating with the conical elements (9) that make it possible to feed the entire annular zone (IIa), a function known as predistribution of the catalyst.

A leg (7) is generally inserted into the corresponding conical part (9) by means of a sliding connection, this connection having to be sealed against the catalyst.

Given that the solid plate (5) closes the gaps left between the conical elements (9), the feedstock introduced into the upper hemispheric body (III) through the pipe (6) passes through the outer screen (3), and then crosses the bed contained in the annular zone (IIa) in an approximately radial manner, after passing through the outer screen (3).

The reaction effluents are collected in the central collector (4) and pass into the lower hemispheric body (I), from where they are drained through the pipe (1).

The connection between the central collector (4) and the outlet pipe (1) is generally accomplished by a flange, but other connection methods are possible while remaining entirely within the scope of the invention.

A perforated pipe (not shown in FIG. 1) is often attached to the central collector (4) for the purpose of improving the gas distribution over the entire height of the reactor while generating an additional pressure drop.

The outer screen (3) can optionally be replaced with a network of scallop elements forming a continuous unit (elements called "scallops" in English terminology).

This invention also relates to a method of assembling the reactor according to the invention that can be described in the following way:

a) the lower body (I) is equipped with drain legs (8) for draining the catalyst, and with a drain pipe (1) for the reaction effluents that is provided at its upper end with a means that makes possible its reattachment to the central collector (4), b) the central collector (4) is positioned in the lateral zone (IIa), and said central collector (4) is attached to the drain pipe (1) for the effluents, c) said central collector (4) is closed at its upper end by a solid plate (5), d) the lower body (I) is attached to the lateral body (II) by an assembly of flanges (B1) and (B2) that are carried by said lateral body (II) and said lower body (I), e) an outer screen (3) or outer screen elements are attached to a supporting ring (2) positioned in the unit formed by the lateral body (II) and the lower body (I), f) the upper body (III) is attached to the lateral body (II) by means of an assembly of flanges (B3) and (B4), said upper body (III) being previously equipped with a pipe (6) for introducing the feedstock and with lowering legs (7) making possible the entry of the catalyst into the reactor.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 15/62,672, filed Dec. 17, 2015 is incorporated by reference herein.

EXAMPLE ACCORDING TO THE INVENTION

The objective is to process a feedstock of 20 t/h, with a density of 5 kg·m$^{-3}$ and with a viscosity of 0.02 mPa·s, through a chamber comprising a catalytic moving bed having the shape of a vertical cylindrical annulus that is bound
  on the interior side by an interior cylindrical screen, defining the central collector (4), and
  on the exterior side by a cylindrical screen (3) of the same type as the interior screen.

After passing through the catalytic bed, the reaction effluents are collected in the vertical cylindrical collector.

The catalyst is in pellet form 2 mm in diameter and with a void rate between the pellets equal to 40%.

The PPH, i.e., the ratio between the feedstock mass flow rate and the weight of catalyst contained in the reactor, is fixed at 50 h$^{-1}$.

Two sizings of the internals are proposed in Table 1, according to the prior art and according to this invention.

The main difference between the sizing of the reactor according to the invention and according to the prior art resides in the constraint in terms of thickness of the catalytic bed (greater than 400 mm according to the prior art).

The volume of the catalyst of 0.6 m3 is the same in both situations.

The operating conditions are the following:
Inlet temperature of the reactor: 520° C.
Average temperature in the reactor: 467° C.
Pressure 0.7 MPa (MPa is the abbreviation for mega pascal or 10$^6$ Pa)

The feedstock is defined by the following characteristics: initial boiling point 80° C., final boiling point 180° C.:
Its distribution in chemical families is given below:

| Feedstock Compositon (% by Weight) | Paraffins | 50 |
|---|---|---|
| | Olefins | 0 |
| | Naphthenes | 40 |
| | Aromatic Compounds | 10 |
| | RON | 45.7 |

The main elements of the sizing are assembled in Table 1 below. Under the operating conditions of the method, it clearly appears that the sizing according to the prior art is not suitable, for the reasons:
- too significant a pressure drop, with multiple consequences, in particular at the level of the operating costs of the method,
- a difficult inspection of the central collector (4) given its small diameter,
- velocities that are too high in the radial bed, which creates a risk of blocking the catalytic flow.

TABLE 1

| | | Prior Art | Reactor According to the Invention |
|---|---|---|---|
| CC Diameter | (m) | 0.3 | 0.5 |
| OS Diameter | (m) | 1.1 | 1.1 |
| Thickness | (m) | 0.4 | 0.3 |
| Height | (m) | 0.68 | 0.80 |
| Inlet Velocity | (m/s) | 0.47 | 0.40 |
| Outlet Velocity | (m/s) | 1.73 | 0.89 |
| PD | (mBars) | 148 | 52 |

In Table 1, the following abbreviations are used:
CC: central collector (4).
OS: outer screen (3).
The thickness is the radial dimension between the outer screen (3) and the central collector (4).
The inlet velocity is taken in the area of the outer screen (3).
The outlet velocity is taken in the area of the central collector (4).
PD: pressure drop in the radial dimension of the catalytic bed from the outer screen (3) to the central collector (4).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A moving-bed reactor having a radial flow of a feedstock and having a gravitational flow of a catalyst comprising an upper hemispheric body (III), a lateral body (II), and a lower hemispheric body (I),
   the upper hemispheric body (III) being provided with an intake pipe (6) for the feedstock and with legs (7) for introducing the catalyst communicating with conical elements (9) that provide access to an annular zone (IIa),
   the annular zone (IIa) is located between a central collector (4) and an outer screen (3) over a radial distance of between 100 mm and 400 mm, said outer screen (3) being positioned parallel to the lateral body (II) of the reactor and at a certain distance from the latter, and the central collector (4) extending approximately along the longitudinal axis of symmetry of the reactor over the entire height of said annular zone (IIa) and continuing inside a lower hemispheric body (I),
   the lower hemispheric body (I) carries drain legs (8) of the catalyst and a drain pipe (1) for the reaction effluents, said drain pipe (1) connected to a lower end of the central collector (4),
   the outer screen (3) being supported by a supporting ring (2), which extends over the entire periphery of the lower hemispheric body (I) and which is attached to the lower hemispheric body (I), and the central collector (4) being closed at its upper end by a solid plate (5),
   wherein the upper hemispheric body (III) is connected by flanges (B3, B4) to the lateral body (II), and the lateral body being furthermore connected by flanges (B1, B2) to the lower hemispheric body (I),
   wherein the flange (B4) and the lower end of the conical element (9) are positioned at the lower end of the upper hemispheric body (III), and
   wherein the flange (B3) and the solid plate (5) are positioned at the upper end of the lateral body (II), and provides access to the annular zone (IIa).

2. The reactor according to claim 1, wherein the outer screen (3) consists of an assembly of scallop-shaped screen elements, extending longitudinally over the entire height of the annular zone (IIa).

3. A method using the reactor according to claim 1, comprising:
   feeding the feedstock into the reactor by the intake pipe (6) located in the upper part of an upper hemispheric body (III) of the reactor and enters into the annular zone (IIa) located inside the lateral body (II) by passing through the outer screen (3),
   moving the feedstock through a catalytic bed contained in the annular zone (IIa) in an approximately radial manner, and the effluents resulting from a catalytic reaction are collected in the central collector (4), and then
   continuously draining the effluents from said reactor through the drain pipe (1) that is reattached to the central collector (4),
   admitting the catalyst into the annular zone (IIa) through legs (7) located in the upper hemispheric body (III) that communicate with said annular zone through conical elements (9), the catalyst flows gravitationally into said annular zone (IIa), and then is drained from the reactor through drain legs (8) located in the lower hemispheric body (I).

4. The method of claim 3 wherein the catalytic reaction is selected from the group consisting of catalytic reforming of gasolines, skeletal isomerization of olefins, metathesis for the production of propylene, oligocracking, and dehydration of alcohols.

5. A method of constructing the reactor according to claim 1, comprising:
   a) equipping the lower hemispheric body (I) with drain legs (8) for draining the catalyst, and with a drain pipe (1) for reaction effluents that is provided at its upper end which is suitable for reattachment to the central collector (4),
   b) positioning the central collector (4) in the annular zone (IIa), and said central collector (4) is attached to the drain pipe (1) for draining the effluents,
   c) closing said central collector (4) at its upper end by a solid plate (5),
   d) attaching the lower hemispheric body (I) to the lateral body (II) by an assembly of flanges (B1) and (B2) carried by said lateral body (II) and said lower hemispheric body (I),
   e) attaching an outer screen (3) or outer screen elements to a supporting ring (2) positioned in a unit formed by the lateral body (II) and the lower hemispheric body (I),
   f) attaching the upper hemispheric body (III) to the lateral body (II) by an assembly of flanges (B3) and (B4), said upper hemispheric body (III) being previously equipped with a intake pipe (6) for introducing the feedstock and with legs (7) making possible the intake of the catalyst into the reactor.

* * * * *